(12) United States Patent
Asaka (10) Patent No.: US 8,160,667 B2
(45) Date of Patent: Apr. 17, 2012

(54) BIOLOGICAL LIGHT MEASURING APPARATUS AND METHOD

(75) Inventor: Hirokazu Asaka, Matsudo (JP)

(73) Assignee: Hitachi Medical Corporation, Tokyo (JP)

( * ) Notice: Subject to any disclaimer, the term of this patent is extended or adjusted under 35 U.S.C. 154(b) by 1727 days.

(21) Appl. No.: 10/580,533

(22) PCT Filed: Nov. 9, 2004

(86) PCT No.: PCT/JP2004/016605
§ 371 (c)(1),
(2), (4) Date: May 25, 2006

(87) PCT Pub. No.: WO2005/051196
PCT Pub. Date: Jun. 9, 2005

(65) Prior Publication Data
US 2007/0135695 A1    Jun. 14, 2007

(30) Foreign Application Priority Data

Nov. 26, 2003  (JP) .................................. 2003-395429

(51) Int. Cl.
*A61B 5/1455* (2006.01)
(52) U.S. Cl. ........................................ 600/323; 600/310
(58) Field of Classification Search .......... 600/309–344, 600/500–502
See application file for complete search history.

(56) References Cited

U.S. PATENT DOCUMENTS

| | | | |
|---|---|---|---|
| 5,786,592 A * | 7/1998 | Hok | 250/227.14 |
| 6,374,128 B1 * | 4/2002 | Toida et al. | 600/310 |
| 6,611,698 B1 | 8/2003 | Yamashita | |
| 2004/0158134 A1 * | 8/2004 | Diab et al. | 600/323 |

FOREIGN PATENT DOCUMENTS

| | | |
|---|---|---|
| EP | 0 549 835 A1 | 7/1993 |
| JP | 11-311599 | 11/1999 |
| JP | 2000-116625 | 4/2000 |
| JP | 2002-224092 | 8/2002 |
| JP | 2003-135434 | 5/2003 |
| WO | WO 02/063282 A1 | 8/2002 |
| WO | WO 03/071935 A1 | 9/2003 |

OTHER PUBLICATIONS

European Search Report dated Aug. 6, 2010, issued in corresponding European Patent Application No. 04819290.
European Office Action, dated Apr. 6, 2011, issued in corresponding European Patent Application No. 04 819 290.0.

* cited by examiner

*Primary Examiner* — Eric Winakur
*Assistant Examiner* — Marjan Fardanesh
(74) *Attorney, Agent, or Firm* — Antonelli, Terry, Stout & Kraus, LLP.

(57) ABSTRACT

An optical fiber setting adequacy evaluation unit is disclosed for evaluating a setting adequacy on a body surface in an inspection area of irradiation use optical fibers. The evaluation unit can also be used for setting the accuracy of light receiving use optical fibers at both ends of respective measurement channels in an optical measurement apparatus for living body. The evaluation unit evaluates the setting adequacy on the body surface of a subject of the irradiation use optical fibers or of light receiving use optical fibers for the respective measurement channels. The evaluation is performed based on pulse wave intensities of the respective measurement channels calculated by a pulse wave calculation unit. The pulse wave calculation unit calculates intensities of the pulse wave due to heartbeats of a subject contained in hemoglobin signals of the respective measurement channels calculated by a hemoglobin signal calculation unit.

15 Claims, 8 Drawing Sheets

BIOLOGICAL LIGHT MEASURING APPARATUS AND METHOD

BACKGROUND OF THE INVENTION

1. Field of the Invention

The present invention relates to an optical measurement apparatus for living body, in particular, an optical measurement apparatus for living body having an improved function of evaluating whether the settings of respective optical fiber probes of a probe device, which is attached to an inspection area of a subject, are adequate and which permits to evaluate correctly whether the settings of the respective optical fibers on a body surface of the subject, and a method thereof.

2. Description of the Related Art

An optical measurement apparatus for living body is an apparatus which permits to measure simply and easily living body information inside a living body, for example, such as blood circulation, hemodynamics and variation of hemoglobin concentration with low restriction to a subject and in a non-invasive manner to the living body through irradiating light having frequencies of from visible to near infrared regions to the living body and detecting the light penetrating through inside the living body.

When performing an optical measurement for living body of a subject representing a living body with the optical measurement apparatus for living body, at first an optical fiber probe device including irradiation use optical fiber probes and light receiving use optical fiber probes which are arranged alternatively at respective lattice points of, for example, 4×4 is attached on an inspection area of the subject, for example, on the headportion. In the case of the optical fiber probe device including irradiation use optical fiber probes and light receiving use optical fiber probes which are arranged alternatively at respective lattice points of 4×4, a total of 24 measurement channels each including a measurement point between respective adjacent irradiation use optical fiber probes and light receiving use optical fiber probes are formed inside the living body of the subject.

FIGS. 2~5 are diagrams showing schematically four manners of settings of mutually adjacent irradiation use optical fiber and light receiving use optical fiber which are set on a body surface of a living body representing a subject and between which a measurement channel including a measurement point is formed.

Figure 2:
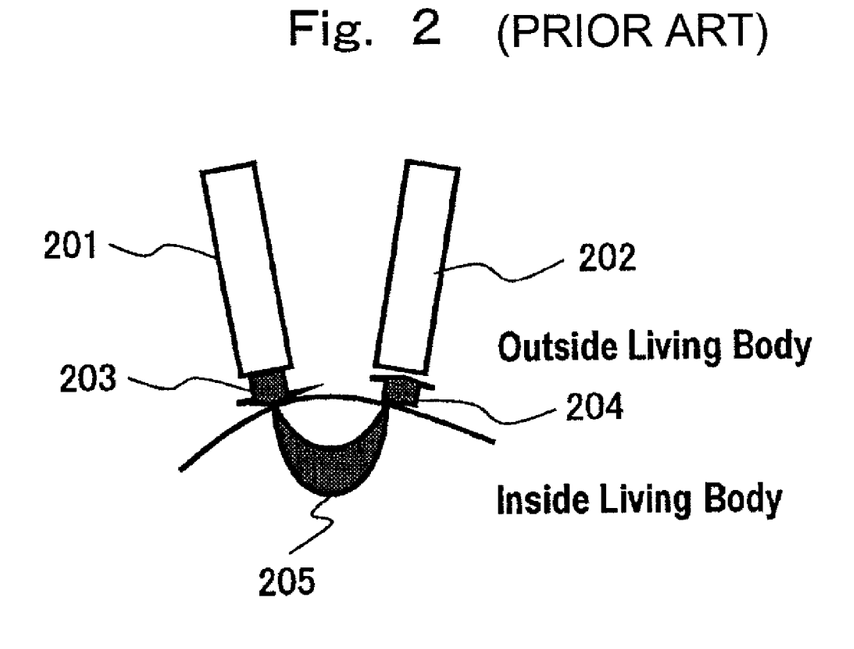
FIG. 2 is a view for explaining a manner of attenuation of inspection light from an irradiation use optical fiber to a light receiving use optical fiber at a measurement channel when the irradiation use optical fiber and the adjacent light receiving use optical fiber are adequately set on a body surface of a living body representing a subject.

FIG. 2 is an example where the setting of the optical fibers is adequate and shows a state in which inspection light 203 irradiated from irradiation use optical fiber 201 passes through inside of living body 205 and light 204 emerged outside from the living body makes incident into light receiving use optical fiber 202. Under this optical fiber setting condition, a sufficient near infrared light, which is subjected to absorption and reflection by hemoglobin inside the living body can be detected.

Figure 3:
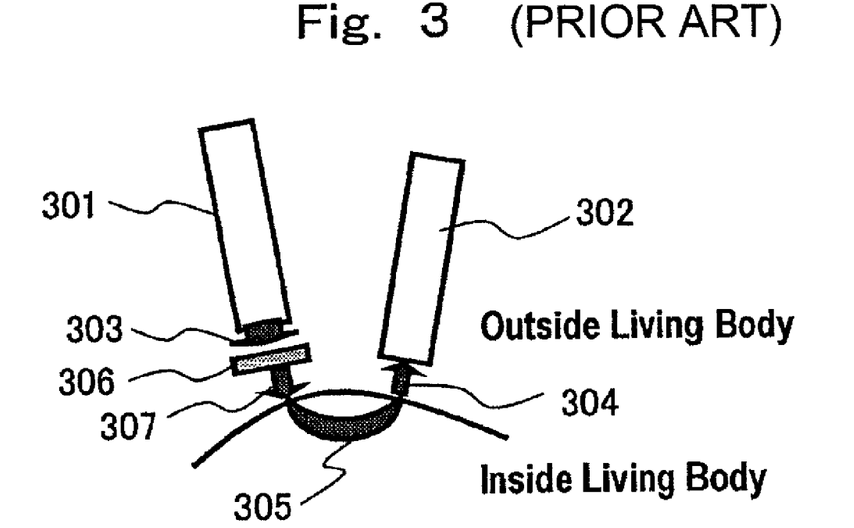
FIG. 3 is a view for explaining a manner of attenuation of inspection light from an irradiation use optical fiber to a light receiving use optical fiber at a measurement channel when the irradiation use optical fiber and the adjacent light receiving use optical fiber are inadequately set on a body surface of a living body representing a subject, in that the irradiation use optical fiber is set remote from the body surface of the living body as well as hair is caught therebetween.

FIG. 3 is an example where the setting of the irradiation use optical fiber is inadequate and shows a state in which inspection light 303 irradiated from an irradiation use optical fiber 301 passes through an obstacle 306 such as hair, light 307 of which intensity is weakened passes through inside living body 305 and penetrating light 304 emerged outside from the living body makes incident into light receiving use optical fiber 302. Under this optical fiber setting condition, since signals of the irradiation light 303 are disturbed by the obstacle 306, sufficient near infrared light subjected to absorption and reflection by hemoglobin inside the living body 305 can not be detected. Further, even in a case when no obstacle 306 such as hair is caught between the irradiation use optical fiber 301 and the surface of the living body, if the irradiation use optical fiber 301 is remote from the surface of the living body and the attenuation of the irradiation light is extreme, since sufficient inspection light which has penetrated through the subject can not be detected, the setting of the optical fiber is evaluated as inadequate.

Figure 4:
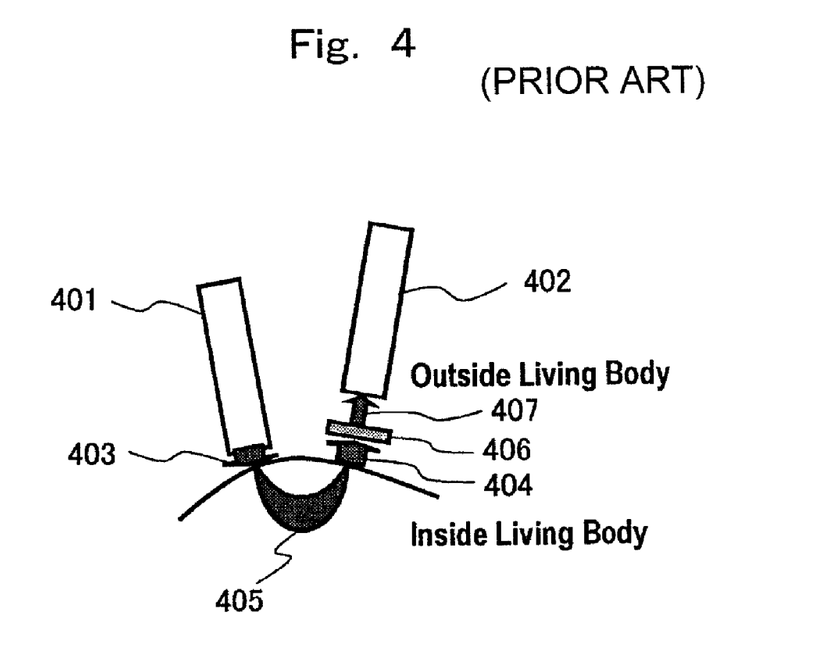
FIG. 4 is a view for explaining a manner of attenuation of inspection light from an irradiation use optical fiber to a light receiving use optical fiber at a measurement channel when the irradiation use optical fiber and the adjacent light receiving use optical fiber are inadequately set on a body surface of a living body representing a subject, in that the light receiving use optical fiber is set remote from the body surface of the living body as well as hair is caught therebetween.

FIG. 4 is an example where the setting of the light receiving use optical fiber is inadequate and shows a state in which irradiation light 403 irradiated from an irradiation use optical fiber 401 passes through inside living body 405 and penetrating light 404 emerged outside from the living body passes through an obstacle 406 such as hair, light 407 of which intensity is weakened makes incident into light receiving use optical fiber 402. Under this optical fiber setting condition, since signals of the penetrating light 404 are disturbed by the obstacle 406, sufficient near infrared light subjected to absorption and reflection by hemoglobin inside the living body 405 can not be detected. Further, even in a case when no obstacle 406 such as hair is caught between the light receiving use optical fiber 401 and the surface of the living body, if the light receiving use optical fiber 402 is remote from the surface of the living body and the attenuation of the irradiation light is extreme, since sufficient inspection light which has penetrated through the subject can not be detected, the setting of the optical fiber is evaluated as inadequate.

Figure 5:
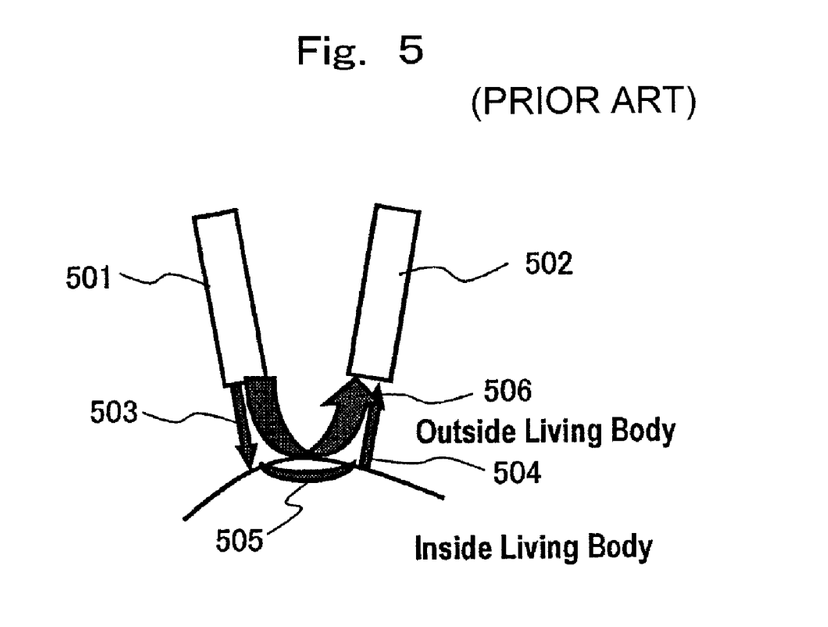
FIG. 5 is a view for explaining a manner of attenuation of inspection light from an irradiation use optical fiber to a light receiving use optical fiber at a measurement channel when the irradiation use optical fiber and the adjacent light receiving use optical fiber are inadequately set on a body surface of a living body representing a subject, in that both irradiation use optical fiber and light receiving use optical fiber are set remote from the body surface of the living body.

FIG. 5 is an example where the setting of both irradiation use and light receiving use optical fibers is inadequate because both are inadequately remote from a living body representing a measurement object and shows a state in which since irradiation use optical fiber 501 is remote from a living body, irradiation light 503 of which intensity is weakened passes through inside living body 505 and penetrating light emerged outside from the living body of which intensity is weakened makes incident into light receiving use optical fiber 502. On the other hand, since the light receiving use optical fiber 502 is also remote from the surface of the living body, light from the irradiation use optical fiber 501 of which intensity is high in comparison with that of the light passed through inside the living body is directly makes incident to the light receiving use optical fiber 502. Under this condition, since the penetrating light 504 passed through inside the living body 505 mixes with the direct light 506 from outside the living body, the amount of received light is much, however, sufficient near infrared light which is subjected to absorption and reflection by hemoglobin inside the living body 505 representing measurement object can not be detected.

In a conventional optical measurement apparatus for living body as, for example, disclosed in JP-A-11-311599, an evaluation and judgment is performed whether the setting of respective pairs of adjacent optical fibers each constituting a measurement channel of a probe device which is attached on a body surface of an inspection area of a subject is adequate or not in such a manner that after setting the respective optical fibers, a short time preparatory measurement is performed prior to beginning an actual measurement, in which gains of irradiation light amount from respective irradiation use optical fibers and received light amount of respective paired light receiving use optical fibers are detected, more specifically, a gain adjustment is performed for the respective measurement channels and for a measurement channel of which gain adjustment has failed the setting of the optical fibers is evaluated and judged as inadequate and resetting work of the optical fibers is performed for the respective concerned channels.

However, with the method as disclosed in the conventional optical measurement apparatus for living body, the inadequate optical fiber setting state as shown in FIG. 5 was evaluated and judged as adequate optical fiber setting because the amount of light received by the light receiving use optical fiber is sufficient, although the amount of light penetrated inside the living body containing hemoglobin signals is insufficient.

For this reason, even though the measurement data of such measurement channels is erroneous measurement data, the erroneous measurement data are treated as correct measurement data, operated and processed, of which result possibly causes an erroneous diagnosis or reduction of diagnosis efficiency.

An object of the present invention is to provide an optical measurement apparatus for living body having a function which performs a correct evaluation and judgment whether the setting of respective pairs of adjacent optical fibers each constituting a measurement channel of a probe device which is attached on a body surface in an inspection area of a subject is adequate or not and a method thereof.

Another object of the present invention is to provide an optical measurement apparatus for living body, which can prevent an erroneous diagnosis or reduction of diagnosis efficiency due to an inadequate setting of respective pairs of adjacent optical fibers each constituting a measurement channel of a probe device which is attached on a body surface in an inspection area of a subject and a method thereof.

SUMMARY OF THE INVENTION

An optical measurement apparatus for living body according to the present invention being provided with a light irradiation means including an irradiation use optical fiber which irradiates light subjected to different modulation from a light irradiation position to a living body, a light detection means including a light receiving use optical fiber which detects light penetrated inside the living body at a detection position and outputs an electrical signal corresponding to the amount of light detected at a measurement portion which is determined in relation to the light irradiation position, a signal processing means which calculates hemoglobin concentration at every measurement portion based on the electrical signal from the light detection means and display means which displays a calculation result of the signal processing means, is characterized in that the signal processing means includes an evaluation and judgment means which evaluates and judges an intensity of pulse wave contained in the hemoglobin signals and performs an evaluation and judgment of adequacy of the setting state of the irradiation use and/or light receiving use optical fiber on the body surface of the living body based on the evaluation and judgment.

Further, the evaluation and judgment means according to the present invention is characterized by performing the evaluation and judgment based on the peak magnitude of a center frequency in the statistic of the hemoglobin signal.

With the optical measurement apparatus for living body according to the present invention, an adequacy of the setting state of the irradiation use and/or light receiving use optical fiber on the body surface of the living body can be correctly evaluated and judged.

With the optical measurement apparatus for living body according to the present invention, since a possible mixture of erroneous measurement data from a measurement channel constituted by a pair of inadequately set irradiation use and light receiving use optical fibers of the probe device is eliminated, an erroneous diagnosis or reduction of diagnosis efficiency can be prevented.

DETAILED DESCRIPTION OF THE INVENTION

Figure 1:
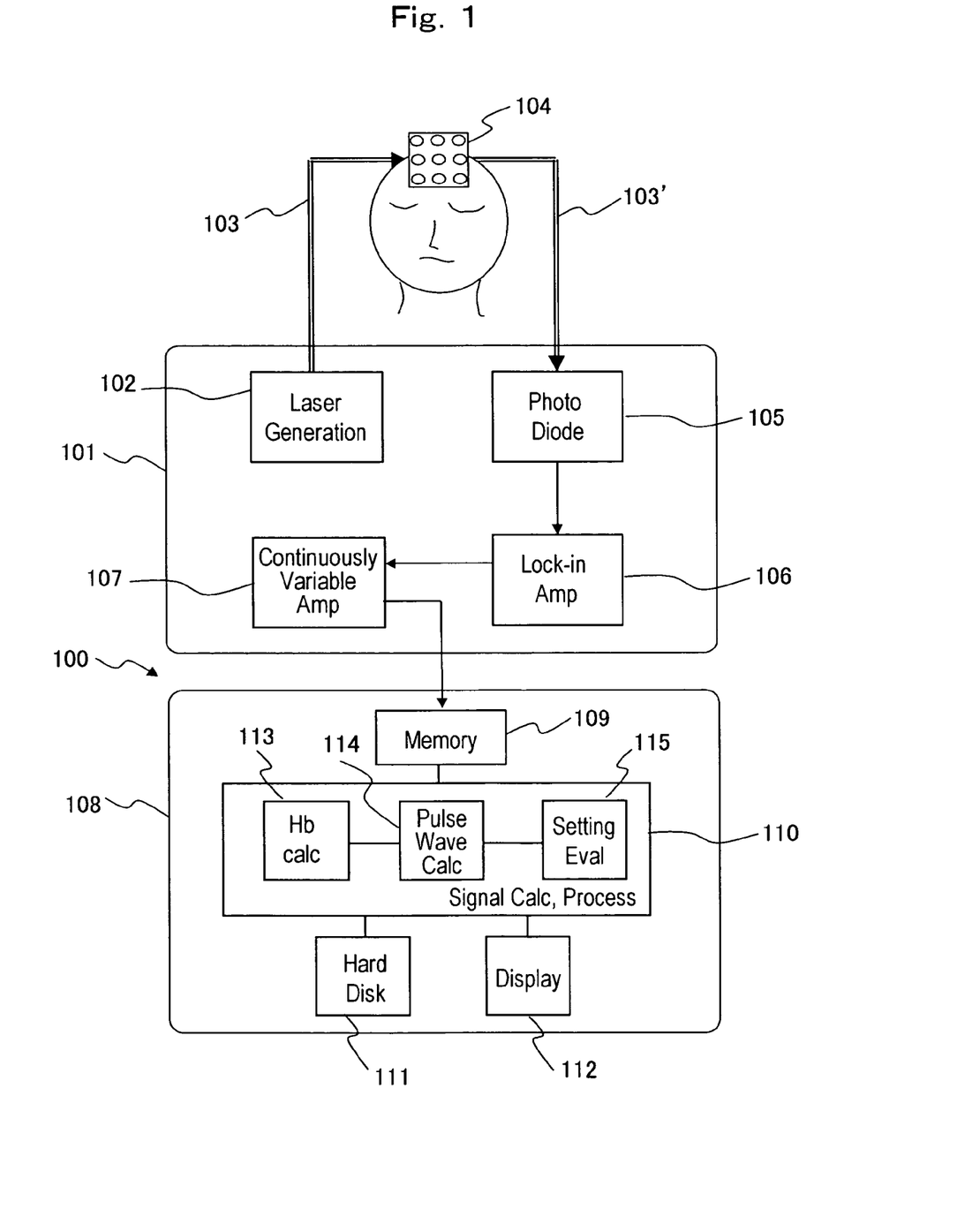
FIG. 1 is a block diagram showing a schematic constitution of an optical measurement apparatus for living body according to the present invention.

Herein below, embodiments of the present invention will be explained in detail. FIG. 1 is a constitutional diagram of an optical measurement apparatus for living body according to the present embodiment. An optical measurement apparatus for living body 100 is constituted by an optical measurement unit for living body 101 and an optical signal for living body calculation and display unit 108, the optical measurement unit for living body 101 includes a laser generation unit 102 which generates near infrared light having frequencies of about 600~1200 nm which easily penetrates through a human body, a fiber unit 103 which guides and irradiates the laser beam generated from the laser generation unit 102, for example, toward a scalp portion, another fiber unit 103' which receives and detects the near infrared light subjected to absorption and reflection by hemoglobin at the brain surface, a probe 104 for attaching the fiber units 103 and 103' to the head portion, an avalanche diode 105 for converting the inputted near infrared light into electrical signals, a lock-in amplifier 106 for amplifying the electrical signals and a continuously variable amplifier 107, and the optical signal for living body calculation and display unit 108 is constituted by a memory 109 for recording the electrical signals from the continuously variable amplifier 107, a central processing unit CPU 110 for converting the electrical signals into hemoglobin signals, a hard disk 111 for recording the hemoglobin signals and a monitor 112 for displaying the hemoglobin signals.

In addition to a hemoglobin signal calculation unit 113, which is provided conventionally, the central processing unit CPU 110 includes a pulse wave calculation unit 114 which calculates pulse wave components due to heartbeats and a setting evaluation unit 115 which evaluates and judges setting adequacy of each pair of an irradiation use optical fiber and a light receiving use optical fiber set at both ends of respective measurement channels, both of which are for realizing the present invention.

Figure 6:
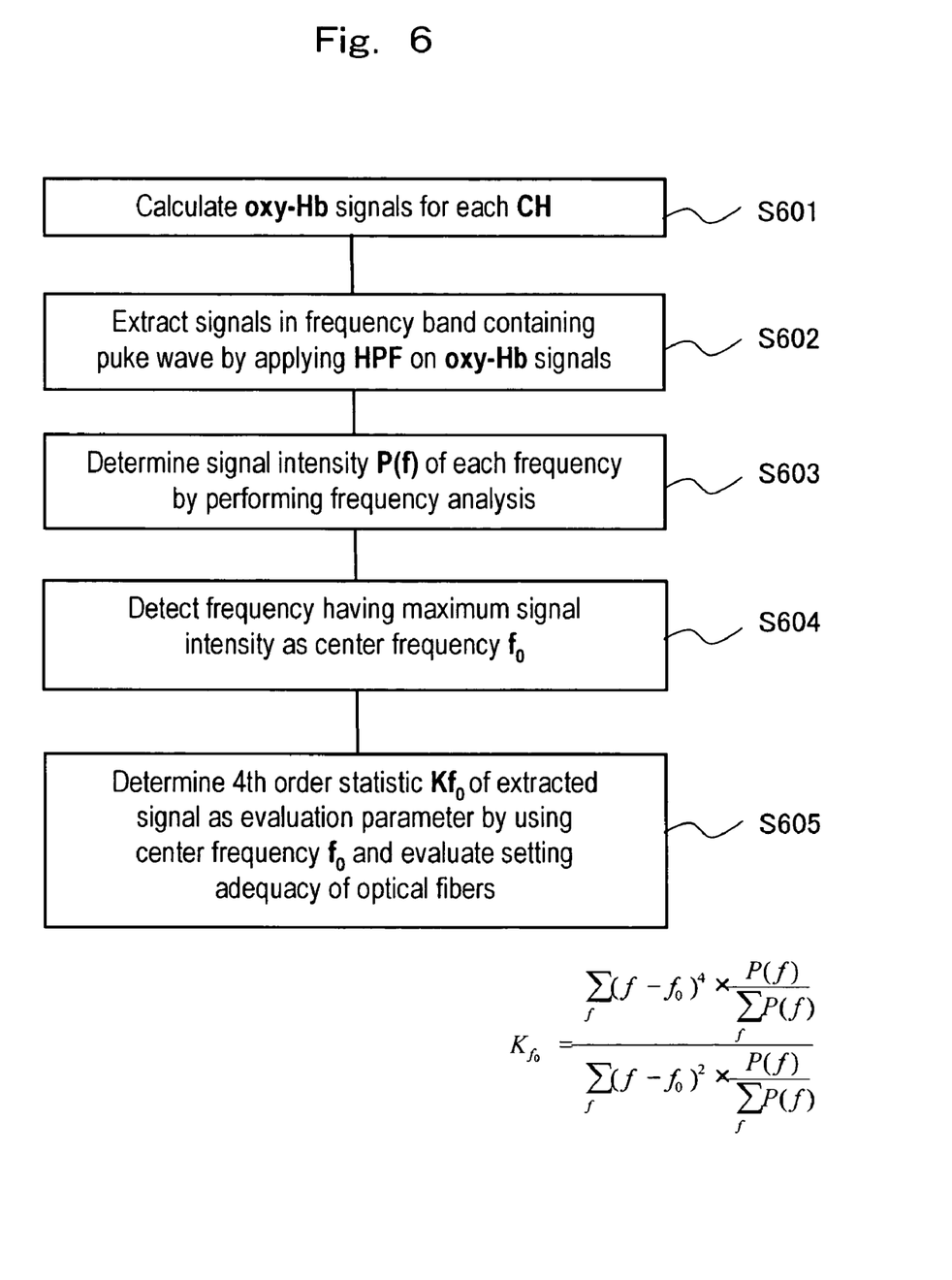
FIG. 6 is a flowchart for explaining a sequence in an embodiment for evaluating setting adequacy of respective pairs of irradiation use optical fibers and light receiving use optical fibers set on the body surface of a living body representing a subject, which is executed in a signal calculation and processing unit of an optical measurement apparatus for living body according to the present invention.

Now, a sequence of evaluating adequacy of a setting state of an irradiation use optical fiber and/or a light receiving use optical fiber on a surface of a living body representing a subject as explained, for example, with reference to FIG. 2~FIG. 5, which is performed with the optical measurement apparatus for living body according to the present invention provided with the pulse wave calculation unit 114 and the setting evaluation unit 115, will be explained according to FIG. 6 flowchart which is one embodiment of the present invention.

At first, at step 601, for example, oxy-Hb values due to hemoglobin oxidation of respective measurement channels for every measurement are determined from the measurement result of the optical measurement for living body. In the present embodiment, although the oxy-Hb values are used, deoxy-Hb values due to deoxidation or total-Hb values relating to total hemoglobin can be used.

Subsequently, at step 602, in order to extract pulse wave components due the heartbeats, a HPF (High frequency band Pass Filter) using a proper frequency value performed by a program provided in the pulse wave calculation unit 114 is applied to the measurement result. Although the HPF (High frequency band Pass Filter) is usually used for the purposes of extracting pulse wave components due the heartbeats and of removing a low frequency band containing target components of the optical measurement for living body, when a component different from the pulse wave component due to heartbeats is contained in the high frequency band, for example, when mixing of noises having a specific frequency is presumed, an LPF (Low Frequency band Pass Filter) or a BPF (Band Pass Filter) performed by a program provided in the pulse wave calculation unit 114 is used. When the subject is a newborn, the frequency component used for the HPF is, for example, 1 Hz. This is because when a subject is a newborn, the pulse wave component due to heartbeats appears in a frequency band of 1.6~2.1 Hz and in a frequency band below 1 Hz living body information inside the living body (for example, such as functional signal representing hemoglobin concentration variation at a specific portion in the brain caused by moving a part of the human body) which is the primary target of the measurement appears. Therefor, in order to extract pulse wave components due the heartbeats it is proper to use a HPF of 1 Hz. Further, when the subject is an adult, it is proper to use a HPF, for example, of 0.5 Hz. However, a band threshold value (which frequency is to be used) for the band pass filter (such as HPF and LPF and a combination thereof) can be arbitrarily input by an operator via an input unit (not shown).

After extracting from the measurement result signal components in the frequency band which are presumed as containing the pulse wave components due the heartbeats at step 602, a frequency analysis is performed with a program provided in the pulse wave calculation unit 114 at step 603 and the signal intensity P(f) for the respective frequency components f is calculated. Then, at step 604 a frequency having the maximum signal intensity among the signal components in the frequency band which are presumed as containing the pulse wave components due the heartbeats is detected as a center frequency fo from the result of performing the frequency analysis.

Subsequently, at step 605 a fourth order statistic Kfo around the detected center frequency fo and as shown in the drawing is calculated and used as a parameter for judging the setting adequacy of optical fibers. The fourth order statistic Kfo represents the peak steepness of the signal intensity at the center frequency fo and when pulse wave signals due to heartbeats are contained many, the value becomes large and when pulse wave signals due to heartbeats are contained less, the value becomes small. Therefore, if the setting of the optical fibers is adequate, since the light used for the measurement passes inside the living body, in particular, through a blood vessel and makes incident to a light receiving use optical fiber, the measurement result always contains the pulse wave signals due to heartbeats. Contrary, if the setting of the optical fibers is inadequate, since the inspection light used for the measurement has not sufficiently passed through the blood vessel inside the living body, the measurement result hardly contains the pulse wave signals due to heartbeats, when the setting of the optical fibers is inadequate.

In the present invention, the signal components relating to the pulse wave due to heartbeats are extracted via the pulse wave calculation unit 114 from the hemoglobin signal information stored in the memory 109 and the hard disk 111 and through calculation and evaluation of the peak magnitude at the center frequency fo of the fourth order statistic Kfo with the setting evaluation unit 115, the judgment of setting adequacy of the optical fibers is enabled. Since the value of fourth order statistic Kfo under normal distribution is 3, when as the threshold value, for example, 3 is used, it is judged that when the fourth order statistic Kfo is more than 3, the setting of the optical fibers is adequate and when less than 3 the setting is inadequate. However, the threshold value can be arbitrarily input by an operator via an input unit (not shown).

Since the judgment of the present invention which uses the magnitude of the value of the fourth order statistic Kfo depends on the amount of inspection light used for the measurement passed through inside the living body, the case (FIG. 2) in which the setting of the optical fibers is adequate and the case (FIG. 5) in which the optical fibers are inadequately remote from the surface of the living body representing the measurement object can be discriminated. Further at the same time, the judgment of the present invention, which uses the magnitude of the value of the fourth order statistic Kfo can discriminate between the case (FIG. 2) in which the setting of the optical fibers is adequate, the case (FIG. 3) in which setting of the irradiation use optical fiber is inadequate and the case (FIG. 4) in which setting of the light receiving use optical fiber is inadequate.

Figure 7:
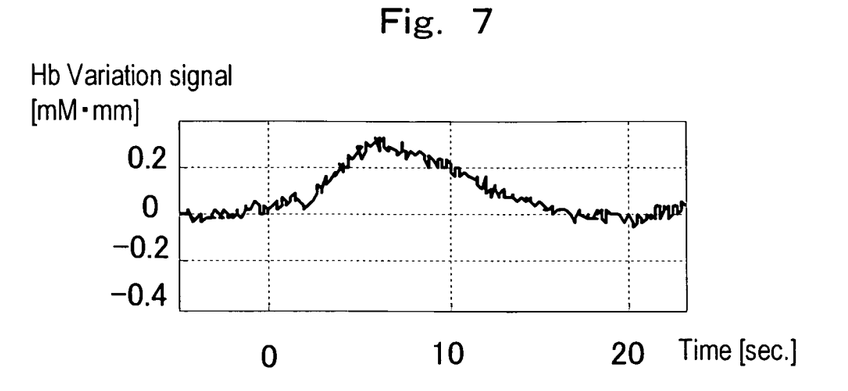
FIG. 7 is a graph showing oxyhemoglobin variation signal calculated according to step 601 in FIG. 6 at a certain channel for which the irradiation use optical fiber and/or the light receiving use optical fiber are adequately set.
Figure 8:
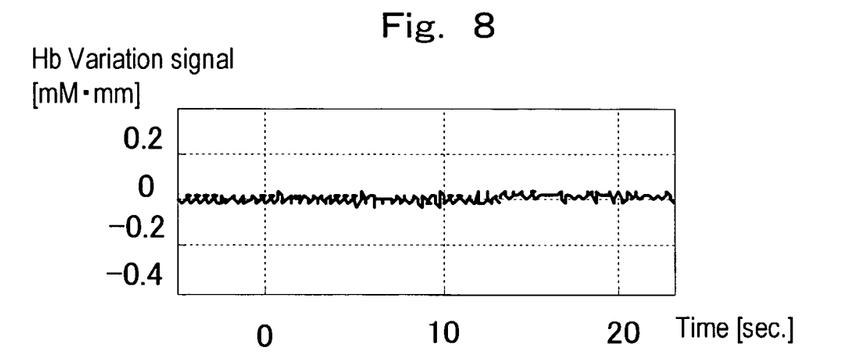
FIG. 8 is a graph showing oxyhemoglobin variation signal in a frequency band containing pulse wave due to heartbeat extracted by applying an HPF (high frequency band pass filter) to the oxyhemoglobin variation signal as shown in FIG. 7 according to step 602 in FIG. 6.
Figure 9:
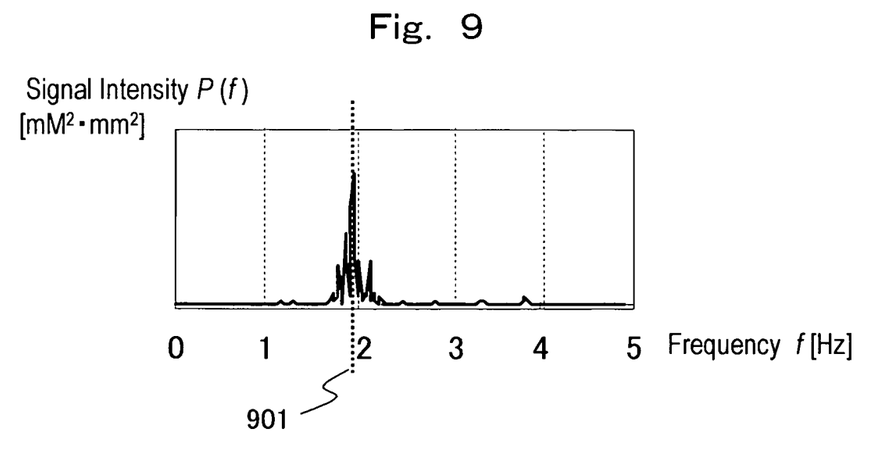
FIG. 9 is a graph showing signal intensity P(f) determined for respective frequencies by performing frequency analysis on the oxyhemoglobin variation signal as shown in FIG. 8 according to step 603 in FIG. 6.

Now, a specific example of hemoglobin signal processing according to FIG. 6 embodiment will be explained. By making use of FIGS. 7~9 a case when a setting of an optical fiber is adequate will be explained. FIG. 7 shows a measurement result of one channel for the optical measurement for living body, which is the result according to step 601 in FIG. 6 flowchart. FIG. 8 is a processed result in which the processing in FIG. 6 step 602, in that the HPF (High frequency band Pass Filter) is applied to the measurement result of one channel for the optical measurement for living body as shown in FIG. 7. FIG. 9 is a processed result in which the processing in FIG. 6 step 603, in that the frequency analysis is performed to the measurement result of one channel for the optical measurement for living body as shown in FIG. 8. According to the processed result as shown in FIG. 9, from signals in the frequency band representing the pulse wave components due to the heartbeats the frequency having the maximum power is detected as the center frequency fo. Since the present example is a measurement result of a newborn, a center frequency (901) of 1.9 Hz is detected among the frequency band signals of 1.6~2.1 Hz.

Since the fourth order statistic Kfo determined by making use of the center frequency fo is 7.43, when the threshold value 3 is used which is the value of fourth order statistic Kfo under normal distribution, the measurement result of the present example contains a substantial amount of pulse wave signals and the setting of the optical fibers is judged as adequate. Further, in an example when the subject is an adult, 0.8~1.2 Hz is used as a frequency band representing pulse wave due to heartbeats.

Figure 10:
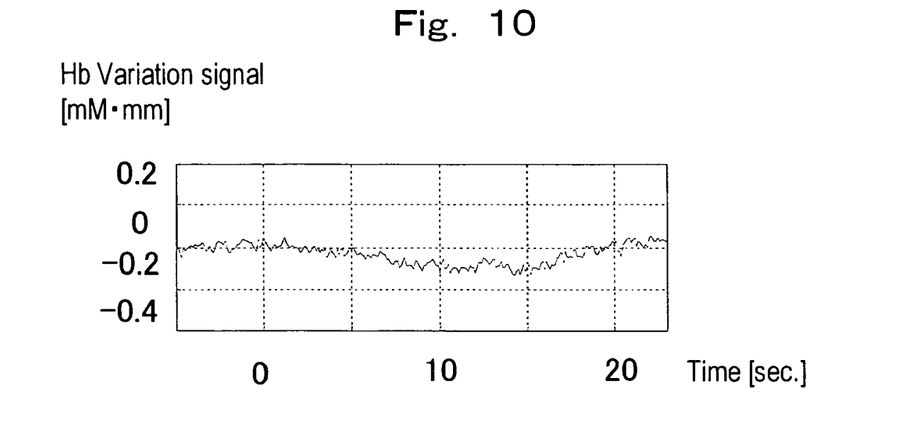
FIG. 10 is a graph showing oxyhemoglobin variation signal calculated according to step 601 in FIG. 6 at another channel for which the irradiation use optical fiber and/or the light receiving use optical fiber are inadequately set.
Figure 11:
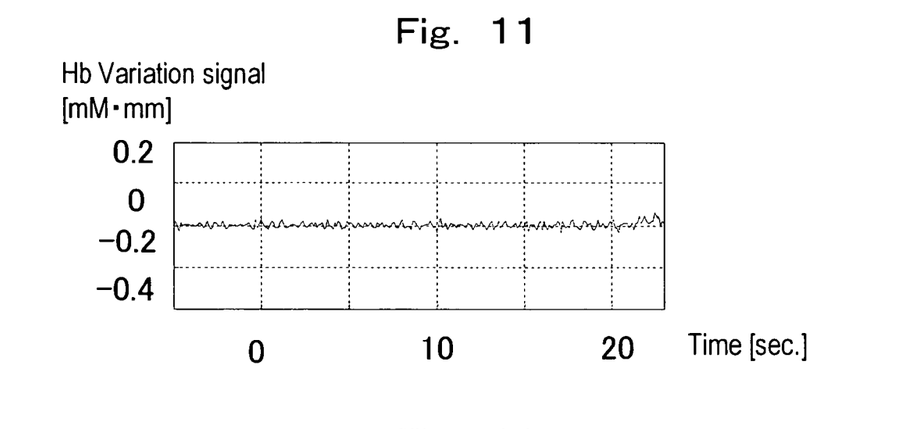
FIG. 11 is a graph showing oxyhemoglobin variation signal in a frequency band containing pulse wave due to heartbeats extracted by applying an HPF (high frequency band pass filter) to the oxyhemoglobin variation signal as shown in FIG. 10 according to step 602 in FIG. 6.
Figure 12:
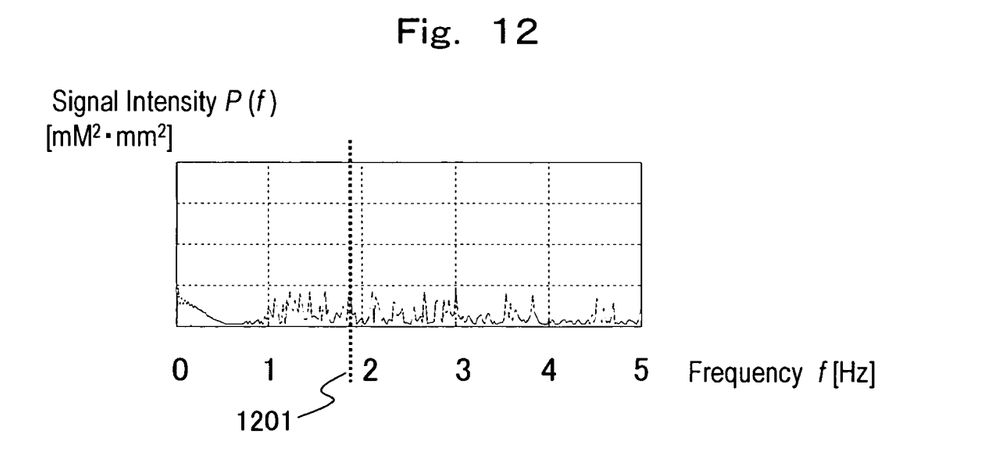
FIG. 12 is a graph showing signal intensity P(f) determined for respective frequencies f by performing frequency analysis on the oxyhemoglobin variation signal as shown in FIG. 11 according to step 603 in FIG. 6.

By making use of FIGS. 10~12 a case when a setting of an optical fiber is inadequate will be explained. FIG. 10 shows a measurement result of another channel than that of FIG. 7 for the optical measurement for living body in an example when the subject is a newborn and which is the result according to step 601 in FIG. 6 flowchart. FIG. 11 is a processed result in which the processing in FIG. 6 step 602, in that the HPF (High frequency band Pass Filter) is applied to the measurement result of one channel for the optical measurement for living body as shown in FIG. 10. Like the processing used in FIG. 8, the frequency component used for the HPF is, for example, 1 Hz in an example when the subject is a newborn. FIG. 12 is a processed result in which the processing in FIG. 6 step 603, in that the frequency analysis is performed to the measurement result of one channel for the optical measurement for living body as shown in FIG. 11. According to the processed result as shown in FIG. 12, from signals in the frequency band representing the pulse wave components due to the heartbeats the frequency having the maximum power is detected as the center frequency fo. Since the present example is a measurement result of a newborn, a center frequency (1201) of 1.8 Hz is detected among the frequency band signals of 1.6~2.1 Hz.

Since the fourth order statistic Kfo determined by making use of the center frequency fo is 2.74, when the threshold value 3 is used which is the value of fourth order statistic Kfo under normal distribution, the measurement result of the present example contains no substantial amount of pulse wave signals and the setting of the optical fibers is judged as inadequate.

Figure 13:
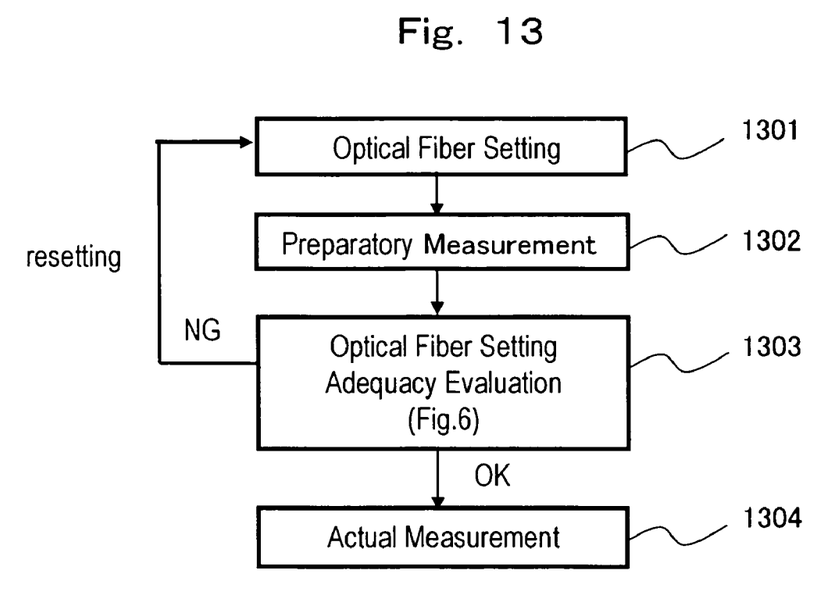
FIG. 13 is a flowchart for explaining a sequence in an embodiment of optical measurement for living body with an optical measurement apparatus for living body according to the present invention having a function of evaluating a setting adequacy of optical fibers for the respective measurement channels as shown in FIG. 6 embodiment.
Figure 14:
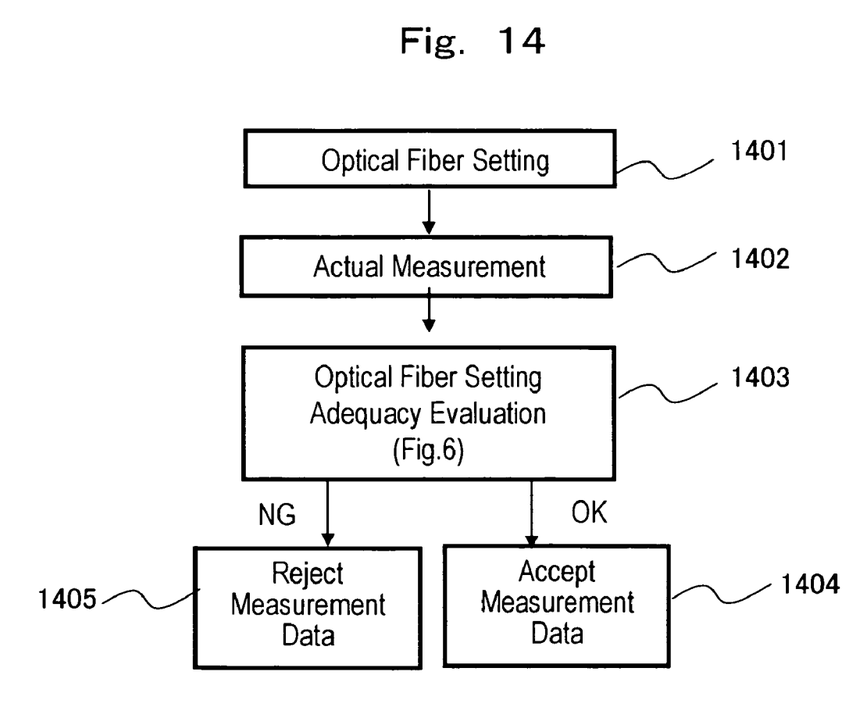
FIG. 14 is a flowchart for explaining a sequence in another embodiment of optical measurement for living body with an optical measurement apparatus for living body according to the present invention having a function of evaluating a setting adequacy of optical fibers for the respective measurement channels as shown in FIG. 6 embodiment.
Figure 15:
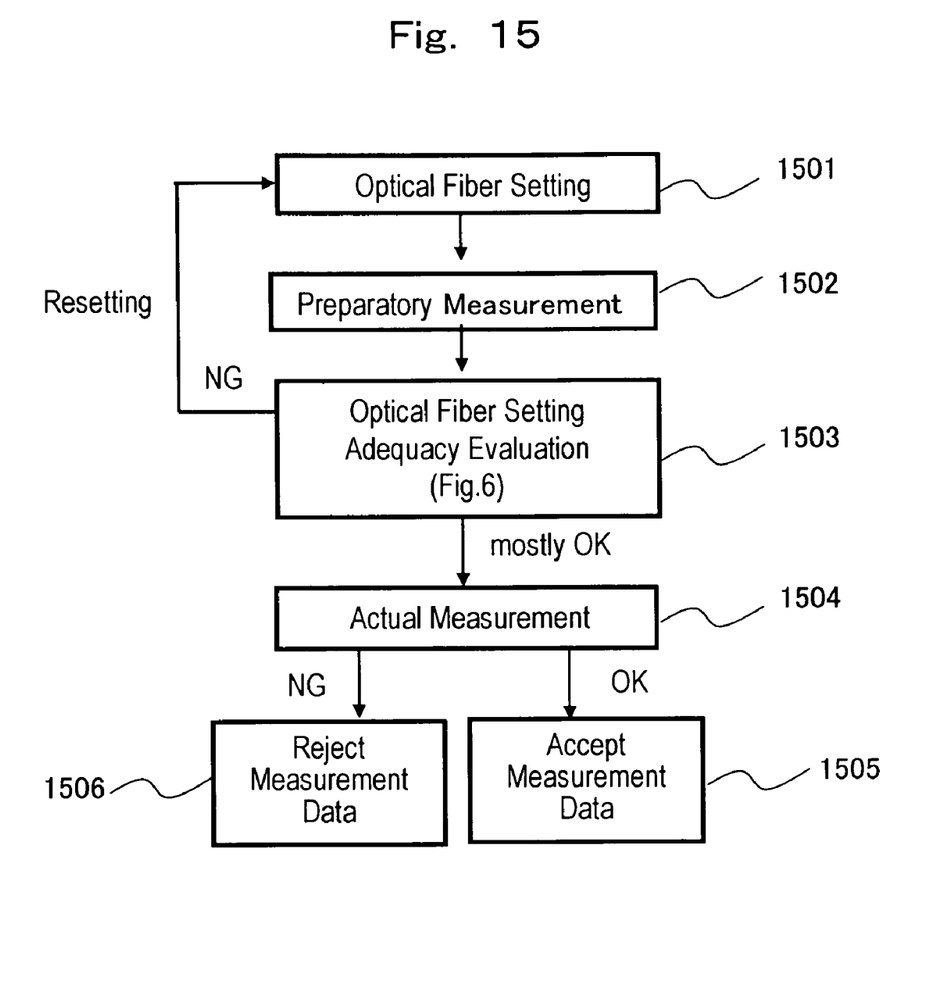
FIG. 15 is a flowchart for explaining a sequence in still another embodiment of optical measurement for living body with an optical measurement apparatus for living body according to the present invention having a function of evaluating a setting adequacy of optical fibers for the respective measurement channels as shown in FIG. 6 embodiment.

FIGS. 13~15 are flowcharts for explaining respective sequences of optical measurement for living body of embodiments of optical measurement apparatus for living body according to the present invention provided with a setting adequacy evaluation and judgment function of the irradiation use optical fibers and/or the light receiving use optical fibers of which function has been explained with reference to FIG. 6 flowchart.

In FIG. 13 embodiment, at first in step 1301, optical fibers are set on the body surface in the inspection area of the subject, subsequently, in step 1302 a short time preparatory measurement of about 10 seconds is performed. Then, in step 1303, by making use of the preparatory measurement at step 1302 the evaluation and judgment according to FIG. 6 on the setting adequacy of the optical fibers is performed for respective measurement channels, and when there are measurement channels of which setting are judged inadequate, the process returns to step 1301, the optical fibers of the measurement channels of which setting are judged inadequate are reset, the steps 1302 and 1303 are repeated, and when no measurement channels of inadequate setting is reached, the process advances to step 1304 of an actual measurement.

In FIG. 14 embodiment, at first in step 1401 like step 1301 in FIG. 13, optical fibers are set on the body surface in the inspection area of the subject, and omitting the preparatory measurement in FIG. 13, at step 1402 the actual measurement is directly performed. After completing the actual measurement, at step 1403, by making use of the actual measurement at step 1402 the evaluation and judgment according to FIG. 6 on the setting adequacy of the optical fibers is performed for respective measurement channels, and the measurement data of measurement channels of which settings are judged adequate are accepted as hemoglobin signals to be used for obtaining living body information inside the living body which is the primary target of the optical measurement for living body at step 1404 and on the other hand, the measurement data of measurement channels of which settings are judged inadequate are rejected as hemoglobin signals to be used for obtaining living body information inside the living body which is the primary target of the optical measurement for living body at step 1405 by a rejecting means.

FIG. 15 is a combination of concepts of the measurement sequences of FIGS. 13 and 14, at first in step 1501, optical fibers are set on the body surface in the inspection area of the subject, subsequently, in step 1502 a short time preparatory measurement of about 10 seconds is performed, then, in step 1503, by making use of the preparatory measurement at step 1502 the evaluation and judgment according to FIG. 6 on the setting adequacy of the optical fibers is performed for respective measurement channels, and when there are measurement channels of which setting are judged inadequate, a simple resetting work such as moving the entire probe a little is performed, and the steps 1502 and 1503 are repeated, and the settings are reached mostly OK, the process advances to step 1504 of an actual measurement. This is for the purpose of avoiding useless long time restriction of the subject by repeating the optical fiber resetting, the preparatory measurement and the setting adequacy evaluation of the optical fibers. After the above process, the measurement data of measurement channels of which settings are judged adequate at the last preparatory measurement are accepted as hemoglobin signals to be used for obtaining living body information inside the living body which is the primary target of the optical measurement for living body at step 1505 and on the other hand, the measurement data of measurement channels of which settings are judged inadequate are rejected as hemoglobin signals to be used for obtaining living body information inside the living body which is the primary target of the optical measurement for living body at step 1506 by a rejecting means. According to FIG. 15 method, even when a setting fault of an optical fiber is caused during the actual measurement, the measurement data from the optical fiber at which the fault is caused are prevented from being accepted as data for obtaining the living body information inside the living body of the subject.

Further, any of the sequences of the optical measurement for living body according to FIGS. 13~15 can be used depending on the condition of the subject.

The present invention is not limited to the above embodiments and can be carried out in a variety of modifications in a range without departing the gist of the present invention. In particular, although the number of the fiber units 103 which guide and irradiate laser beams to the scalp portion and of the fiber units 103' which receive and detect the reflected near infrared light are not explained in the present embodiments, the number thereof is of course can be either single or plural.

The invention claimed is:

1. An optical measurement apparatus for living body comprising:
 a measurement channel including an irradiation use optical fiber which is set at an irradiation position on a body surface in an inspection area of a subject and irradiates an inspection light having a predetermined frequency of from visible to near infrared range and a light receiving use optical fiber which is set at a light receiving portion adjacent the irradiation use optical fiber on the body surface in the inspection area and receives the inspection light irradiated from the adjacent irradiation use optical fiber and penetrated through inside the subject;
 a light detection unit which detects the amount of inspection light received by the light receiving use optical fiber in an electrical signal; and
 a signal calculation and processing unit including a hemoglobin signal calculating unit which calculates a hemoglobin signal representing a hemoglobin concentration inside the subject through which the inspection light has penetrated based on the electrical signal detected by the light detection unit and an optical fiber setting adequacy evaluation unit which evaluates adequacy of setting on the body surface in the inspection area of the irradiation use optical fiber or the light receiving use optical fiber both of which constitute the measurement channel,
 wherein:
  the signal calculation and processing unit further includes a pulse wave calculation unit which calculates an intensity of a pulse wave component due to heartbeats of the subject contained in the hemoglobin signal calculated by the hemoglobin signal calculation unit,
  the optical fiber setting adequacy evaluation unit evaluates adequacy of setting on the body surface of the subject of the irradiation use optical fiber or the light receiving use optical fiber based on the intensity of the pulse wave component calculated by the pulse wave calculation unit, and
  the intensity of the pulse wave component calculated by the pulse wave calculation unit is an intensity at the center frequency among the pulse wave component.

2. An optical measurement apparatus for living body according to claim 1, characterized in that a plurality of the measurement channels are included and are constituted by a plurality of the irradiation use optical fibers and a plurality of the light receiving use optical fibers.

3. An optical measurement apparatus for living body according to claim 1 or 2, characterized in that the pulse wave calculation unit is provided with means for applying a band pass filter to the hemoglobin signal calculated by the hemoglobin signal calculation unit and means for performing frequency analysis on the data applied of the band pass filter, and the intensity of the pulse wave component is calculated based on the data performed of the frequency analysis.

4. An optical measurement apparatus for living body according to claim 3, characterized in that the band pass filter is a high frequency band pass filter, a low frequency band pass filter or a combination thereof.

5. An optical measurement apparatus for living body according to claim 3, characterized in that further comprises means for inputting a band threshold value for the band pass filter by an operator.

6. An optical measurement apparatus for living body according to claim 1 or 2, characterized in that the optical fiber setting adequacy evaluation unit evaluates the setting adequacy of the irradiation use optical fiber and/or the light receiving use optical fiber on the body surface of the subject based on whether the intensity of the pulse wave component calculated is larger than or smaller than the predetermined threshold value.

7. An optical measurement apparatus for living body according to claim 6, characterized in that further comprises means for inputting the predetermined threshold value for the intensity of the pulse wave component by an operator.

8. An optical measurement apparatus for living body according to claim 1 or 2, characterized in that the calculation of the intensity of the pulse wave component by the pulse wave calculation unit and the evaluation of the setting adequacy of the irradiation use optical fibers and/or the light receiving use optical fibers for the respective measurement channels based on the calculation by the optical fiber setting adequacy evaluation unit are performed during a preparatory measurement prior to an actual optical measurement for the living body and a resetting is performed for an irradiation use optical fiber and/or a light receiving use optical fiber of a measurement channel of which setting is evaluated inadequate by the optical fiber setting adequacy evaluation unit.

9. An optical measurement apparatus for living body according to claim 1 or 2, characterized in that further comprises means for rejecting after the actual measurement a hemoglobin signal for obtaining living body information inside the living body of a measurement channel for which resetting of the irradiation use optical fiber or light receiving use optical fiber on the body surface has been performed is evaluated inadequate regardless to the performance of the resetting of the irradiation use optical fiber or light receiving use optical fiber.

10. An optical measurement apparatus for living body according to claim 1 or 2, characterized in that the evaluation of the setting adequacy of the irradiation use optical fiber or the light receiving use optical fiber on the body surface is performed after completing the actual optical measurement for living body which is for obtaining the living body information inside the living body of the subject, and further comprises means for rejecting a hemoglobin signal for obtaining the living body information inside the living body for a measurement channel of which setting is evaluated inadequate by the optical fiber setting adequacy evaluation unit.

11. An optical measurement apparatus for living body comprising:
   a measurement channel including an irradiation use optical fiber which is set at an irradiation position on a body surface in an inspection area of a subject and irradiates an inspection light having a predetermined frequency of from visible to near infrared range and a light receiving use optical fiber which is set at a light receiving portion adjacent the irradiation use optical fiber on the body surface in the inspection area and receives the inspection light irradiated from the adjacent irradiation use optical fiber and penetrated through inside the subject;
   a light detection unit which detects the amount of inspection light received by the light receiving use optical fiber in an electrical signal; and
   a signal calculation and processing unit including a hemoglobin signal calculating unit which calculates a hemoglobin signal representing a hemoglobin concentration inside the subject through which the inspection light has penetrated based on the electrical signal detected by the light detection unit and an optical fiber setting adequacy evaluation unit which evaluates adequacy of setting on the body surface in the inspection area of the irradiation use optical fiber or the light receiving use optical fiber both of which constitute the measurement channel,
   wherein:
      the signal calculation and processing unit further includes a pulse wave calculation unit which calculates an intensity of a pulse wave component due to heartbeats of the subject contained in the hemoglobin signal calculated by the hemoglobin signal calculation unit,
      the optical fiber setting adequacy evaluation unit evaluates adequacy of setting on the body surface of the subject of the irradiation use optical fiber or the light receiving use optical fiber based on the intensity of the pulse wave component calculated by the pulse wave calculation unit,
      the intensity of the pulse wave component calculated by the pulse wave calculation unit is fourth order statistics around the center frequency among the pulse wave component.

12. A method of optical measurement for living body comprising:

(1) step of irradiating inspection light having a predetermined wavelength of from visible to near infrared range with an irradiation use optical fiber set at an irradiation position on a body surface in an inspection area of a subject;
(2) step of receiving the inspection light which is irradiated from the adjacent irradiation use optical fiber and penetrated through inside the subject with a light receiving use optical fiber at a light receiving position adjacent the irradiation use optical fiber on the body surface in the inspection area;
(3) step of detecting the amount of the inspection light received by the light receiving use optical fiber in a form of electrical signal;
(4) step of calculating a hemoglobin signal representing hemoglobin concentration inside the subject through which the inspection light has penetrated based on the detected electrical signal; and
(5) step of evaluating setting adequacy on the body surface in the inspection area of the irradiation use optical fiber or the light receiving use optical fiber,
wherein the step (5) includes:
   (6) step of calculating an intensity of a pulse wave component due to heartbeats of the subject contained in the hemoglobin signal calculated in the step (4), and
   (7) step of evaluating a setting adequacy on the body surface of the subject of the irradiation use optical fiber or the light receiving use optical fiber based on the intensity of the pulse wave component calculated in the step (6), and
wherein the intensity of the pulse wave component calculated in the step (6) is an intensity at the center frequency among the pulse wave component.

13. A method of optical measurement for living body according to claim 12 characterized in that the setting adequacy evaluation on the body surface of the irradiation use optical fiber or the light receiving use optical fiber are performed during a preparatory measurement prior to an actual optical measurement for living body which is for obtaining the living body information inside the living body of the subject and a resetting is performed for an irradiation use optical fiber and/or a light receiving use optical fiber of a measurement channel of which setting is evaluated inadequate by the optical fiber setting adequacy evaluation step.

14. A method of optical measurement for living body according to claim 13, characterized in that further comprises step of rejecting after the actual measurement a hemoglobin signal for obtaining living body information inside the living body of a measurement channel for which the resetting of the irradiation use optical fiber or light receiving use optical fiber on the body surface has been performed is evaluated inadequate regardless to the performance of the resetting of the irradiation use optical fiber and/or light receiving use optical fiber.

15. A method of optical measurement for living body according to claim 12, characterized in that the evaluation of the setting adequacy of the irradiation use optical fiber or the light receiving use optical fiber on the body surface is performed after completing the actual optical measurement for living body which is for obtaining the living body information inside the living body of the subject, and further comprises step of rejecting a hemoglobin signal for obtaining the living body information inside the living body for a measurement channel of which setting is evaluated inadequate by the optical fiber setting adequacy evaluation step.

* * * * *